(12) United States Patent (10) Patent No.: US 12,272,721 B2
Yasuda et al. (45) Date of Patent: Apr. 8, 2025

(54) OPTICAL ELEMENT AND OPTICAL CONCENTRATION MEASURING APPARATUS

(71) Applicant: Asahi Kasei Microdevices Corporation, Tokyo (JP)

(72) Inventors: Daiki Yasuda, Tokyo (JP); Takaaki Furuya, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 313 days.

(21) Appl. No.: 17/652,280

(22) Filed: Feb. 24, 2022

(65) Prior Publication Data

US 2022/0268693 A1 Aug. 25, 2022

(30) Foreign Application Priority Data

Feb. 25, 2021 (JP) .................................. 2021-029058
Jan. 14, 2022 (JP) .................................. 2022-004671

(51) Int. Cl.
*H01L 27/15* (2006.01)
*G01N 33/00* (2006.01)
(Continued)

(52) U.S. Cl.
CPC ....... *H01L 27/156* (2013.01); *G01N 33/0027* (2013.01); *H01L 24/05* (2013.01);
(Continued)

(58) Field of Classification Search
CPC ............... G01N 33/0027; G01N 21/01; G01N 2021/0112; G01N 21/35–3504;
(Continued)

(56) References Cited

U.S. PATENT DOCUMENTS

2001/0015443 A1\* 8/2001 Komoto .................. H01L 33/62
257/81
2005/0225973 A1 10/2005 Eliashevich et al.
(Continued)

FOREIGN PATENT DOCUMENTS

CN 105745765 A 7/2016
CN 109075184 A 12/2018
(Continued)

*Primary Examiner* — Amar Movva
*Assistant Examiner* — Eric Manuel Mulero Flores
(74) *Attorney, Agent, or Firm* — KENJA IP LAW PC (57) ABSTRACT

Provided is an optical element, in which: an internal wiring portion electrically connects a first contact electrode portion and a second contact electrode portion to each other; a second region, an active layer and a second conductive semiconductor layer form a mesa structure; a pad electrode is placed so as to cover a plurality of unit elements, and is electrically connected to at least one of the first contact electrode portion and the second contact electrode portion; a first insulating portion is placed between the pad electrode and a first region of a side surface of a mesa structure and a first conductive semiconductor layer; and a diameter of a circle circumscribed to a region where the pad electrode and a connection portion are in contact with each other is 15% or more of a length of a short side of a substrate.

16 Claims, 11 Drawing Sheets

(51) Int. Cl.
*H01L 23/00* (2006.01)
*H01L 27/144* (2006.01)

(52) U.S. Cl.
CPC .............. *H01L 27/1446* (2013.01); *H01L 2224/04042* (2013.01); *H01L 2224/05019* (2013.01); *H01L 2224/05558* (2013.01); *H01L 2924/10332* (2013.01); *H01L 2924/12041* (2013.01); *H01L 2924/12043* (2013.01)

(58) Field of Classification Search
CPC ....... G01N 21/3518; G01N 2021/3509; G01N 2021/3513; G01N 2021/3522–355; H01L 24/05; H01L 24/06; H01L 24/48; H01L 27/1446; H01L 2224/04042; H01L 2224/05019; H01L 2224/05558; H01L 2224/05624; H01L 2224/05644; H01L 2224/05647; H01L 2224/05655; H01L 2224/05666; H01L 2224/05669; H01L 2224/05671; H01L 2224/0603; H01L 2224/13144; H01L 2224/45099; H01L 2924/00014; H01L 2924/10332; H01L 2924/12041; H01L 2924/12043; H01L 33/08; H01L 33/30; H01L 33/62; H01L 33/38–387; H01L 25/0753; H01L 27/156; H01L 2224/73265; H01L 2224/73251; H01L 2224/48247; H01L 2224/48253; H01L 2224/48257; H01L 24/49; H01L 33/44; H01L 33/52–56; H01L 2933/005; H01L 24/00–98; H01L 31/02021–02027; H01L 27/14643–14663; H01L 2224/00–98; H01L 33/647

See application file for complete search history.

(56) References Cited

U.S. PATENT DOCUMENTS

| | | | |
|---|---|---|---|
| 2010/0148190 | A1 | 6/2010 | Kim et al. |
| 2011/0108862 | A1 | 5/2011 | Horng et al. |
| 2013/0234170 | A1* | 9/2013 | Lim ..................... H01L 27/153 257/88 |
| 2016/0284921 | A1 | 9/2016 | Fujimoto |
| 2017/0154921 | A1 | 6/2017 | Kim et al. |
| 2017/0331004 | A1 | 11/2017 | Fujimori et al. |
| 2019/0051805 | A1 | 2/2019 | Oh et al. |
| 2021/0013369 | A1* | 1/2021 | Han ..................... H01L 33/0075 |

FOREIGN PATENT DOCUMENTS

| | | |
|---|---|---|
| CN | 110061027 A | 7/2019 |
| JP | H11233891 A | 8/1999 |
| JP | 2000019108 A | 1/2000 |
| JP | 2009522803 A | 6/2009 |
| JP | 2010177286 A | 8/2010 |
| JP | 2011258917 A | 12/2011 |
| JP | 2012212743 A | 11/2012 |
| JP | 2017216435 A | 12/2017 |
| JP | 2019009438 A | 1/2019 |
| JP | 6530652 B2 | 6/2019 |
| KR | 1020080088940 A | 10/2008 |

* cited by examiner

OPTICAL ELEMENT AND OPTICAL CONCENTRATION MEASURING APPARATUS

CROSS-REFERENCE TO RELATED APPLICATION

This application claims priority to and the benefit of Japanese Patent Application Nos. 2021-029058 (filed on Feb. 25, 2021) and 2022-004671 (filed on Jan. 14, 2022), the entire contents of which are incorporated herein by reference.

TECHNICAL FIELD

The present invention relates to optical elements and optical concentration measuring apparatuses.

BACKGROUND

In general, infrared rays having a long wavelength of 2 µm or more are used in gas sensors due to the effect of infrared absorption by gases. In particular, in the region of a wavelength from 2.5 µm to 10 µm, there are many absorption bands specific to various types of gases, which is a wavelength band suitable for gas sensors (an example of an optical concentration measuring apparatus). A non-dispersive infrared optical concentration measuring apparatus is known that measures the gas concentration by detecting the absorption amount by using the fact that the wavelength of the infrared rays absorbed differs depending on the type of gas.

For example, in the optical concentration measuring apparatus disclosed in PTL 1, in a gas cell, the light emitted by a light emitting portion is incident on a light receiving portion via a light guide member, and at that time, the gas to be measured is introduced into the gas cell, and the concentration of the gas to be measured is detected according to the output signal of the light receiving portion.

At this time, the larger the amount of light reaching the light receiving region of the light receiving portion from the light emitting portion is, the larger the detection signal can be taken, and thus the signal noise ratio is improved. As a result, the gas concentration can be detected with high accuracy. Thus, in the optical concentration measuring apparatus, it is important to design the light emitting portion, the light receiving portion, and the light guide member as a single unit so as to efficiently guide all of the infrared rays from the light emitting portion to the light receiving portion.

Further, in the optical concentration measuring apparatus, lamps as light emitting elements and thermal elements such as pyroelectric sensors and thermopiles as light receiving element have been used so far. In recent years, Surface Mount Device (SMD) type mid-infrared LEDs and photodiodes have been developed, mass-produced, and used, and gas sensors are being miniaturized.

CITATION LIST

Patent Literature

PTL 1: JP6530652 (B2)

SUMMARY

Technical Problem

In recent years, use of LEDs as light emitting elements and use of photodiodes as light receiving elements have been increasing. However, since it is necessary to provide a pad electrode on a semiconductor chip for connecting wiring for applying a drive current or taking out a signal, the light emitting and light receiving regions are rectangular in shape with the corners missing due to existing the pad electrode region. Further, with the trend toward miniaturization of gas sensors in recent years, the optical elements become reduced in size, and the ratio of the pad electrode region to the chip size of the optical element has been increasing. The region of the light receiving region where the sensitivity does not change in response to a change in the position of the image of the light collected by the light collecting portion is the largest circle Cd that can be defined inside the light receiving region described below. Further, the size of the image formed by the light emitting region projected on the light receiving region is smaller than the size of the image formed by the light emitting region of the smallest circle Ce that can be defined by including the light emitting region described later. Thus, it is necessary that the image of the circle Ce is smaller than the circle Cd in order to prevent the deformation due to heat and the characteristic fluctuation due to the variation in element mounting in the production process. Therefore, the shapes of the light emitting region and the light receiving region are important, but the difficulty of optical path design is increasing along with the demand for smaller chip sizes.

In light of the aforementioned circumstances, it would be thus helpful to provide an optical element that realizes a gas sensor with high fluctuation resistance while increasing the effective light receiving region or light emitting region without increasing the chip size.

Solution to Problem

An optical element according to an embodiment of the present invention comprises a substrate, a plurality of unit elements, an internal wiring portion, a pad electrode and a first insulating portion, the unit elements having:

a first conductive semiconductor layer including a first region and a second region placed on the substrate;

an active layer placed on the second region of the first conductive semiconductor layer;

a second conductive semiconductor layer placed on the active layer;

a first contact electrode portion on the first region of the first conductive semiconductor layer; and a second contact electrode portion on the second conductive semiconductor layer, wherein the internal wiring portion electrically connects the first contact electrode portion of one of the unit elements and the second contact electrode portion of another unit element;

the second region, the active layer and the second conductive semiconductor layer form a mesa structure;

the pad electrode is placed so as to cover the unit elements, and is electrically connected to at least one of the first contact electrode portion and the second contact electrode portion; and the first insulating portion is placed between the pad electrode and the first region of a side surface of the mesa structure and the first conductive semiconductor layer.

The optical element further comprises a connection portion provided on the pad electrode to electrically connect to the outside and electrically connected to the pad electrode, wherein a diameter of a circle circumscribed to a region where the pad electrode is in contact with the connection portion is 15% or more of a length of a short side of the substrate.

An optical concentration measuring apparatus according to an embodiment of the present invention comprises:

the optical element, which is a light receiving element in which a surface on a side on which the first conductive semiconductor layer of the substrate is not placed is a light incident surface;

a light emitting element; and a light guide portion that guides light emitted by the light emitting element to the light receiving element, wherein the light guide portion has a light collecting portion.

The optical concentration measuring apparatus detects, on the basis of a detection signal output from the light receiving element, concentration of an object to be measured interposed in an optical path formed by the light guide portion.

The optical concentration measuring apparatus according to an embodiment of the present invention comprises:

a light receiving element;

the optical element, which is a light emitting element in which a surface on a side on which the first conductive semiconductor layer of the substrate is not placed is a light emitting surface; and a light guide portion that guides light emitted by the light emitting element to the light receiving element, wherein the light guide portion has a light collecting portion.

The optical concentration measuring apparatus detects, on the basis of a detection signal output from the light receiving element, concentration of an object to be measured interposed in an optical path formed by the light guide portion.

Advantageous Effect

According to the present invention, an optical element that realizes a gas sensor having high fluctuation resistance while increasing an effective light receiving region or light emitting region without increasing the chip size can be provided.

DETAILED DESCRIPTION

The embodiments of the present invention will be described below with reference to the drawings. In the following drawings, the same or similar reference signs are assigned to the same or similar portions. However, the drawings are schematic. For example, the relationship between the thickness and the plane dimension is different from the actual one. Further, the following embodiments exemplify an apparatus for embodying the technical idea of the present invention, and do not limit the material, shape, structure, arrangement, etc. of the components to those described below. The technical idea of the present invention can be modified in various ways within the technical scope specified by the claims described in the scope of claims.

Figure 1:
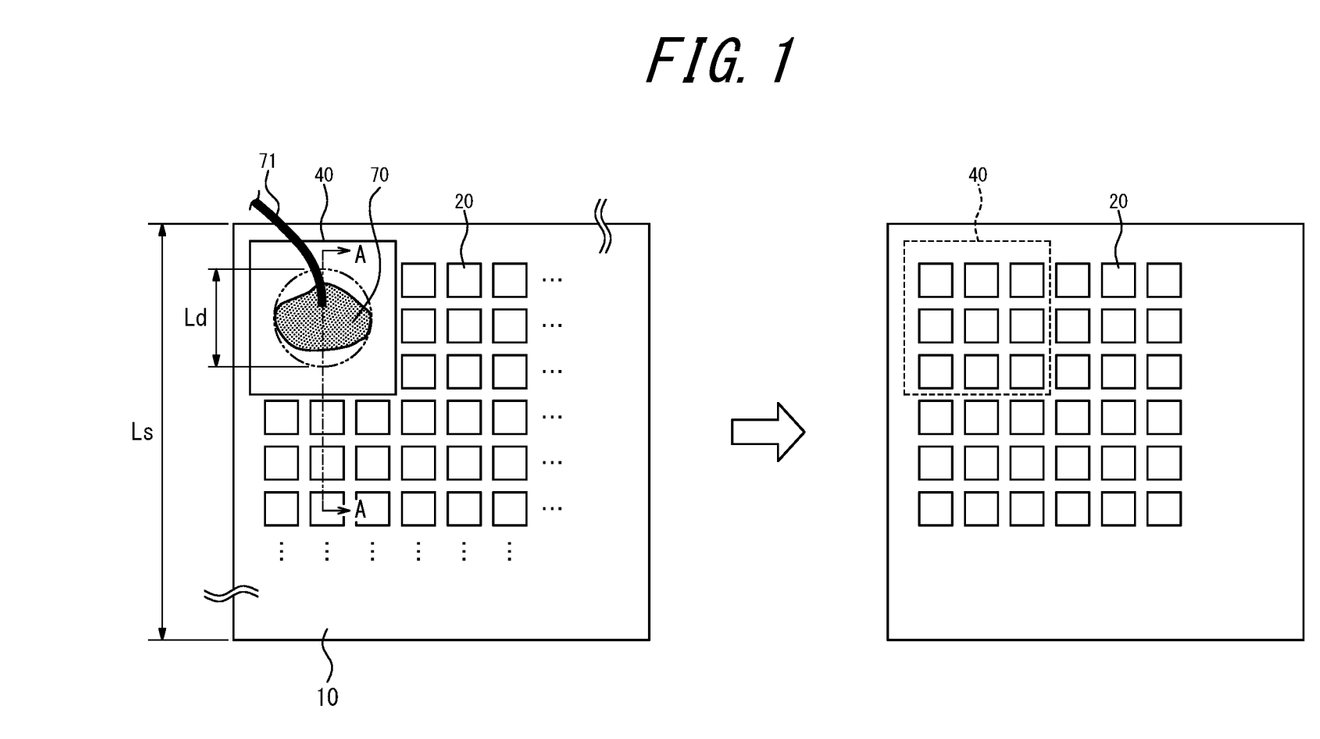
FIG. 1 is a schematic configuration diagram (bird's-eye view) of an optical element according to a first embodiment.
Figure 2:
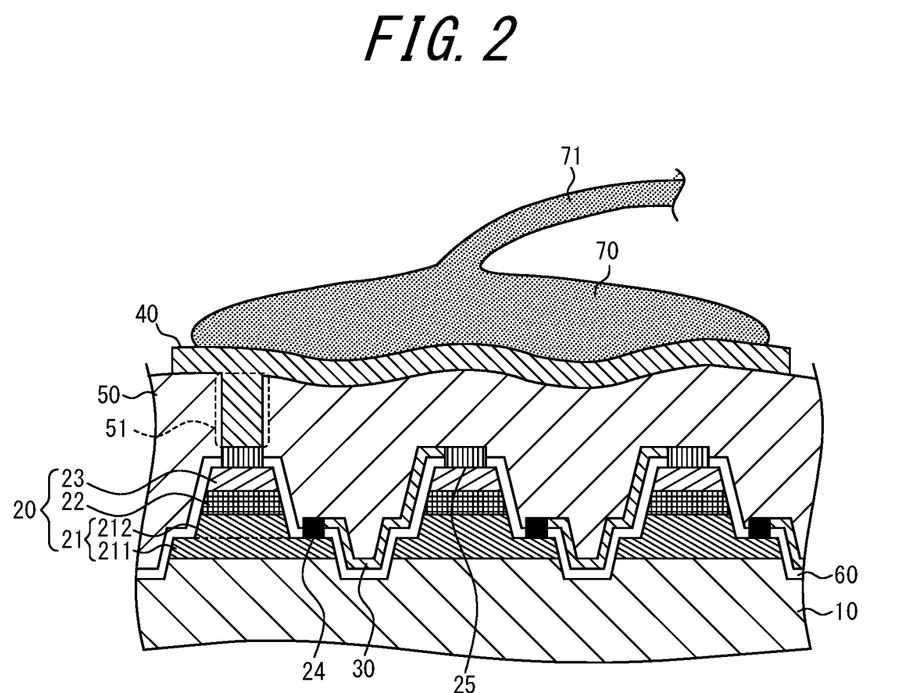
FIG. 2 is a cross-sectional view of the optical element in FIG.1.

FIG. 1 is a schematic configuration diagram of an optical element according to a first embodiment of the present invention. FIG. 1 is a bird's-eye view. FIG. 2 is a cross-sectional view taken along the line A-A illustrated in FIG.1. The optical element comprises a substrate 10, a plurality of unit elements 20, an internal wiring portion 30, a pad electrode 40 and a first insulating portion 50. The unit element 20 has a first conductive semiconductor layer 21, an active layer 22, a second conductive semiconductor layer 23, a first contact electrode portion 24 and a second contact electrode portion 25. Here, a second region 212 of the first conductive semiconductor layer 21, the active layer 22 and the second conductive semiconductor layer 23 form a mesa structure. As illustrated in FIG. 2, a plurality of unit elements 20 are connected by the internal wiring portion 30, and covered by the first insulating portion 50. In FIG. 1, the internal wiring portion 30 and the first insulating portion 50 are not illustrated.

The internal wiring portion 30 electrically connects the first contact electrode portion 24 of one of the unit elements 20 and the second contact electrode portion 25 of another unit element 20. The unit element 20 further comprises a second insulating portion 60 so as not to electrically connect the side surface of the mesa structure to the internal wiring portion 30 in a direct manner.

The second contact electrode portion 25 and the pad electrode 40 are electrically connected to each other through a through hole 51 on the second contact electrode portion 25 of the first insulating portion 50. The pad electrode 40 is placed on the first insulating portion 50 so that it covers a plurality of unit elements 20. The first insulating portion 50 is placed between the pad electrode 40 and a first region 211 of the side surface of the mesa structure and the first conductive semiconductor layer 21. The pad electrode 40 in the example of FIG. 2 corresponds to a second pad electrode 40B (connected to the second contact electrode portion 25) of the second embodiment described later. Here, the pad electrode 40 may correspond to a first pad electrode 40A (connected to the first contact electrode portion 24) of the second embodiment described later.

The optical element according to the first embodiment further comprises a connection portion 70 and connection wiring 71 for electrically connecting to the outside of the optical element.

Further, the diameter Ld of the circle circumscribed to the region where the connection portion 70 is in contact with the pad electrode 40 is 15% or more of the length of the short side Ls of the substrate 10.

[Substrate]

The substrate 10 of this embodiment is not restricted by doping with donor impurities or acceptor impurities. However, from the viewpoint of enabling a plurality of independent unit elements 20 formed on the substrate 10 to be connected in series or in parallel, it is desirable that the substrate is semi-insulating or can be insulated and separated from the first conductive semiconductor layer 21.

When the optical element of this embodiment is a light receiving element, the surface on the side of the substrate 10 on which the first conductive semiconductor layer 21 is not placed does not have the pad electrode 40, so it is preferable to use this side as a light incident surface. When the optical element of this embodiment is a light emitting element, the surface on the side of the substrate 10 on which the first conductive semiconductor layer 21 is not placed does not have the pad electrode 40, so it is preferable to use this side as a light emitting surface.

At this time, since the light is incident on or emitted from the side of the substrate 10, it is necessary to use a material having a band gap larger than that of the active layer 22 as the substrate 10. Examples of the substrate 10 include, but are not limited to, a GaAs substrate, a Si substrate, an InP substrate, and an InSb substrate.

[Mesa Structure]

The optical element of this embodiment comprises the first conductive semiconductor layer 21 including the first region 211 and the second region 212 placed on the substrate 10, the active layer 22 placed on the second region 212 of the first conductive semiconductor layer 21 and the second conductive semiconductor layer 23 placed on the active layer 22. The second region 212, the active layer 22 and the second conductive semiconductor layer 23 form a mesa structure.

The mesa structure is not particularly limited as long as it includes a photodiode structure with a PN junction or a PIN junction. The first conductive semiconductor layer 21 and the second conductive semiconductor layer 23 are opposite conductive types. For example, if the first conductive semiconductor layer 21 is a p-type, the second conductive semiconductor layer 23 is an n-type. For example, if the first conductive semiconductor layer 21 is an n-type, the second conductive semiconductor layer 23 is a p-type. Materials of the first conductive semiconductor layer 21 and the second conductive semiconductor layer 23 include, but are not limited to, InSb, InAsSb, AlInSb, and the like. Further, the first conductive semiconductor layer 21 and the second conductive semiconductor layer 23 may have a laminated structure composed of a plurality of materials.

The active layer 22 preferably contains In and Sb as constituent elements. Narrow bandgap semiconductors containing In and Sb are materials with extremely low resistance. Thus, when used as an LED, in order to realize an appropriate drive voltage and current, a large number of unit elements 20 described later are often connected in series or in parallel. Further, when used as a photodiode, in order to realize a resistance value that is easy to handle when amplifying the output signal by an amplifier circuit, a large number of unit elements 20 described later are often connected in series or in parallel.

At this time, the pad electrode 40 is placed so as to cover the unit elements 20 as in the optical element of this embodiment.

[Contact Electrode]

The optical element according to this embodiment comprises the first contact electrode portion 24 placed on the first region 211 of the first conductive semiconductor layer 21 and the second contact electrode portion 25 placed on the second conductive semiconductor layer 23. It is preferable that the constituent material of the contact electrode has low contact resistance to the semiconductor layer and low electrical resistance. Specifically, examples of the material include Ti, Ni, Pt, Cr, Al, Cu, Au and the like. Further, the contact electrode may be composed of a laminate of a plurality of electrode materials.

[Unit Element]

The optical element according to this embodiment comprises a plurality of unit elements 20 having the first conductive semiconductor layer 21, the active layer 22, the second conductive semiconductor layer 23, the first contact electrode portion 24 and the second contact electrode portion 25.

Further, the unit elements 20 may be electrically connected in series or in parallel. The unit elements 20 are placed two-dimensionally on the substrate 10. The convex polygonal shape having the smallest area including all of the unit elements 20 in a plan view has the same shape as that of the substrate 10 or a shape with one corner missing.

[Internal Wiring Portion]

The optical element according to this embodiment comprises an internal wiring portion 30 that electrically connects the first contact electrode portion 24 of one of the unit elements 20 and the second contact electrode portion 25 of another unit element 20. A plurality of unit elements 20 are electrically connected in series by the internal wiring portion 30. Furthermore, there may be a plurality of unit elements 20 electrically connected in parallel by wiring different from the internal wiring portion 30. As a constituent material of the internal wiring portion 30, it is preferable that the electric resistance is low. Specific examples of the material include Ti, Ni, Pt, Cr, Al, Cu, Au, and the like, and the internal wiring portion may be formed together with the contact electrode.

[Second Insulating Portion]

The unit element 20 of the optical element according to this embodiment may further comprise the second insulating portion 60 such that the side surface of the mesa structure is not electrically connected to the internal wiring portion 30 in a direct manner. The second insulating portion 60 is placed between the first region 211 of the mesa structure and the first conductive semiconductor layer 21, and the internal wiring portion 30. Examples of the constituent material of the second insulating portion 60 include silicon nitride, silicon oxide, aluminum oxide, and the like, but not limited to them. The second insulating portion 60 may be composed of laminate made of a plurality of materials.

[Light Receiving Region]

Figure 8:
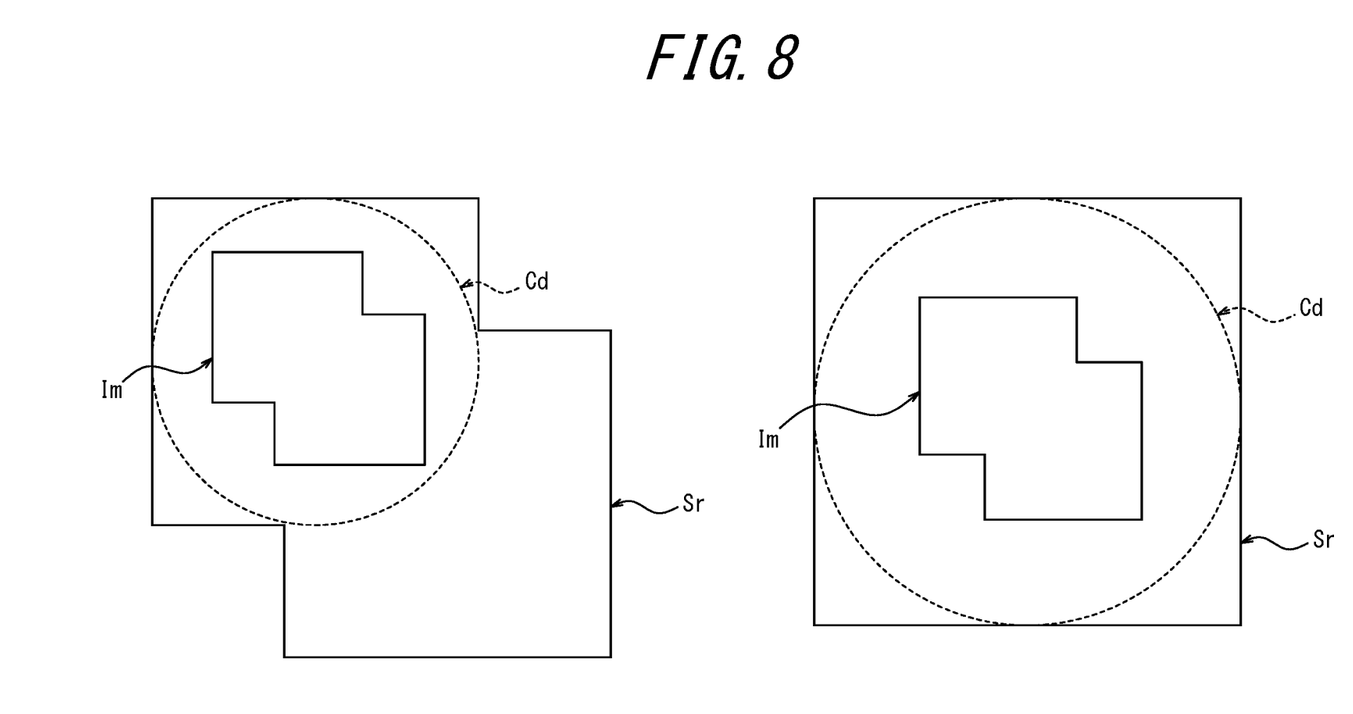
FIG. 8 is a diagram illustrating a relationship between a light receiving region and a circle Cd.

When the optical element of this embodiment is a light receiving element, the region where the light receiving element receives light is referred to as a light receiving region. More specifically, the light receiving region, which has a convex polygonal shape that includes all of the unit elements 20 and has the smallest area in a bird's-eye view of the substrate 10 viewed from a distance in the direction perpendicular to the substrate 10. The light emitted from the light emitting region, which is described later, is collected on the light receiving region by the light collecting portion, and the shape of the light emitting region is formed, as an image Im of the light, on the light receiving region. Further, as illustrated in FIG. 8, the largest virtual circle that can be defined inside the light receiving region Sr is hereinafter referred to as a circle Cd. On the light receiving region Sr, in order not to fluctuate the sensitivity with respect to the change in the position of the image Im of the light caused by the deformation due to heat and variation in mounting of devices in the production process, the image Im of light should be smaller than the minimum length of the diameter of the light receiving region Sr (where the diameter is the smallest width that is perpendicular to the outer frame of the polygon). However, this is equivalent the image Im of light is located in the circle Cd. In other words, in order to design a gas sensor having high fluctuation resistance, the image Im of light should be contained in the circle Cd, and the larger the size of the circle Cd, the higher the fluctuation resistance of the gas sensor can be realized. With such a gas sensor, an optical path can be designed easily. Here, the shape of the image Im of light in FIG. 8 is an example, and does not show the shape of the image of light when the optical element according to this embodiment is used.

[Light Emitting Region]

Figure 9:
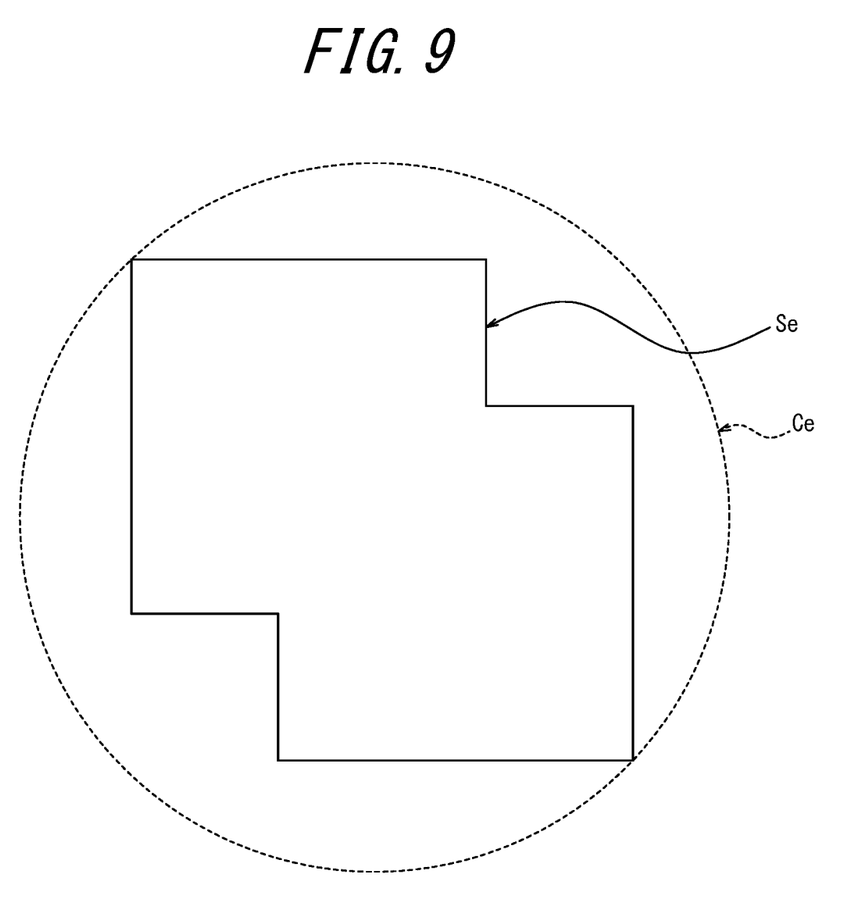
FIG. 9 is a diagram illustrating a relationship between a light emitting region and a circle Ce.
Figure 10:
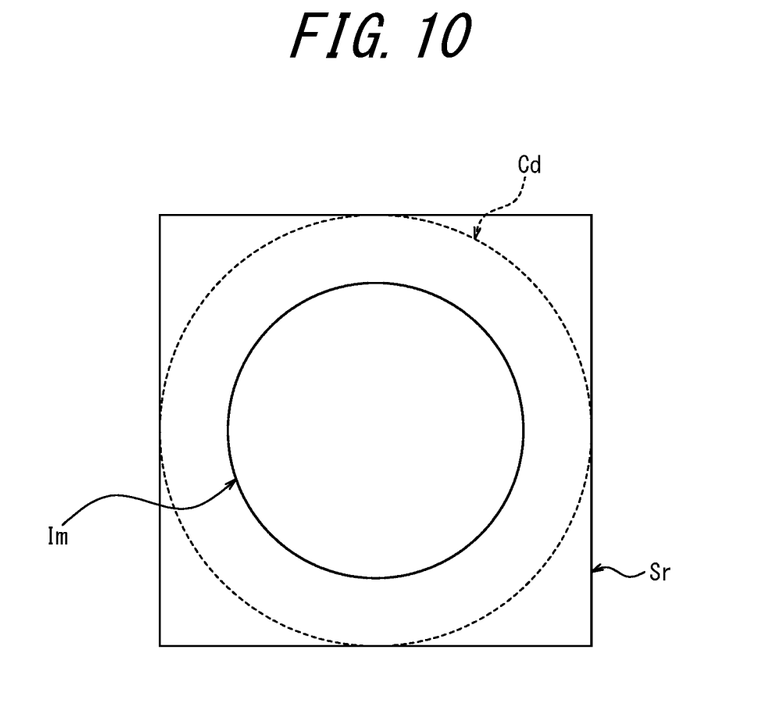
FIG. 10 is a diagram illustrating a relationship between the light receiving region and an image of light formed by the circle Ce.

When the optical element of this embodiment is a light emitting element, the region where the light emitting element emits light is referred to as a light emitting region. More specifically, the light emitting region, which spreads above the substrate 10, has a convex polygonal shape that includes all of the unit elements 20 and has the smallest area in a bird's-eye view of the substrate 10 viewed from a distance in the direction perpendicular to the substrate 10. Further, as illustrated in FIG. 9, the smallest virtual circle that can be defined by including the light emitting region Se is hereinafter referred to as a circle Ce. The size of the image of the light projected on the light receiving region Sr, the light being collected by the light collecting portion formed by the light emitting region Se, is smaller than the image of the light by the two points which are generally the most distant on the light emitting region Se (that is, two end points that define the largest diameter), thus the image is smaller than that formed by the light emitting region of the shape of the circle Ce. Thus, in order to design so as not to fluctuate the sensitivity against the fluctuation of the position, as illustrated in FIG. 10, the light emitting region in the shape of the circle Ce should contain the image Im of the light formed on the light receiving region Sr in the circle Cd. At this time, the larger the area of the light emitting region Se, the larger the amount of light the light emitting element can obtain. Therefore, the larger the area of the light emitting region Se with respect to the circle Ce, the higher the fluctuation resistance of the gas sensor can be realized. With such a gas sensor, a light path can be designed easily. Here, in the rectangular substrate 10, the area of the light emitting region Se is the largest in the case of a rectangle inscribed in the circle Ce. Here, the shape of the light emitting region Se in FIG. 9 is an example, and does not show the shape of the light emitting region Se when the optical element according to this embodiment is used.

[First Insulating Portion]

As described above, the optical element of this embodiment comprises the first insulating portion 50 placed between the pad electrode 40 and the first region 211 of the side surface of the mesa structure and the first conductive semiconductor layer 21. The first insulating portion 50 has a role of not electrically connecting the pad electrodes 40 to the contact electrode portions (the first contact electrode portion 24 and the second contact electrode portion 25) of the unit elements 20 that are not electrically connected to the pad electrode 40 in a direct manner and the internal wiring portion 30. Therefore, the first insulating portion 50 needs to be made of an insulating material. Examples of the material include, but are not limited to, silicon nitride, silicon oxide, aluminum oxide and the like. The material of the first insulating portion 50 may be a resin. Further, the first insulating portion 50 may be composed of a laminate made of a plurality of materials.

The first insulating portion 50 does not necessarily have to be formed to be thicker than the mesa structure as illustrated in FIG. 1. The first insulating section 50 may be an insulating layer having a uniform film thickness, for example. The first insulating section 50 has a function of insulating the pad electrode 40 from the contact electrode and the internal wiring section 30. Here, the contact electrode is a contact electrode of the plurality of unit elements 20 that is not electrically connected to the pad electrode 40 in a direct manner.

[Pad Electrode]

The optical element of this embodiment comprises the pad electrode 40 electrically connected to at least one of the first contact electrode portion 24 and the second contact electrode portion 25. The pad electrode 40 is placed so that it covers a plurality of unit elements 20. The pad electrode 40 is electrically connected to the outside via the connection portion 70. For example, the connection portion 70 and the connection wiring 71 may be wire bonded to each other. Other methods include a flip chip bonding of the connection portion 70 as conductive adhesive or Au bump.

The pad electrode does not need to completely cover two or more unit elements 20, and may be placed so that the size of the pad electrode viewed from above is larger than the size of the unit element 20, and may cover an area of 50% or more of at least two or more unit elements 20. Preferably, the pad electrode is placed so that it covers an area of 80% or more of two or more unit elements 20.

Further, the pad electrode 40 has an uneven shape corresponding to the shape of the mesa structure. More specifically, when viewed from above, a portion of the pad electrode 40 where overlaps the mesa structure is a convex portion and, in a plan view, a portion between one mesa structure and another is a concave portion. Furthermore, the connection portion 70 connected to the pad electrode 40 has an uneven shape. Therefore, since the adhesive area between the pad electrode 40 and the connection portion 70 is increased, the connection portion is more resistive against the lateral force, and reliability is expected to be improved. Here, the maximum difference in height of the pad electrode 40 is preferably 0.5 µm or more and 8 µm or less. More preferably, it is 1 µm or more and 6 µm or less.

The constituent material of the pad electrode 40 may preferably have a low electric resistance, and specific examples thereof include Ti, Ni, Pt, Cr, Al, Cu, Au and the like as in the case of the contact electrode. The pad electrode 40 may be composed of materials different from those of the contact electrode.

[Through Hole]

In the optical element of this embodiment, the contact electrode portion and the pad electrode 40 are electrically connected to each other via the through hole 51 on the contact electrode portion of the first insulating portion 50. The through hole 51 is formed so that it passes through the first insulating portion 50. Further, the inside of the through hole 51 does not necessarily have to be filled with metal as illustrated in FIG. 1, and metal may be formed on the inner surface of the through hole 51 as long as the pad electrode 40 and the contact electrode are electrically connected to each other.

[Connection Portion]

The optical element of this embodiment further comprises the connection portion 70 for electrically connecting to the outside. Specific examples of the connection portion 70 include metal and conductive adhesive. The optical element may be electrically connected to the outside through wire bonding of the connection portion 70 and the connection wiring 71 onto the pad electrode 40. Further, the connection portion 70 may be flip chip bonded as conductive adhesive or Au bump.

The connection portion 70 is bonded to the pad electrode 40. The diameter Ld of the circle that is circumscribed to the region where the connection portion 70 is in contact with the pad electrode 40 needs to be large enough, because if it is small with respect to the size of the substrate 10, damage to the substrate 10 will occur due to concentration of the impact force applied during the bonding process. Preferably, the diameter Ld is 15% or more of the length of the short side Ls of the substrate 10. More preferably, the diameter Ld is 20% or more of the length of the short side Ls. Here, the diameter Ld is preferably 90% or less of the short side Ls, and more preferably 80% or less, from the viewpoint of insulation with other members.

[Light Guide Portion]

The light guide portion is a member that guides the light emitted by the light emitting element to the light receiving element, and is an optical system of the optical concentration measuring apparatus. The light guide portion comprises a light collecting portion, and collects the light emitted from the light emitting region of the light emitting element on the light receiving region of the light receiving element. Specific examples of the light collecting portion include an elliptical mirror, a concave mirror, a lens, a diffraction grating, and the like. The light guide portion may further comprise a flat mirror, a convex mirror, and the like.

[Optical Concentration Measuring Apparatus]

The optical concentration measuring apparatus comprises a light emitting element, a light receiving element that receives light emitted from the light emitting element and converts it into a detection signal, and a light guide portion that guides the light emitted from the light emitting element to the light receiving element. The light guide portion further comprises a light collecting portion. The detection signal is an electrical signal that changes according to the amount of light received. The optical concentration measuring apparatus detects, on the basis of the detection signal output from the light receiving element, the concentration of the object to be measured interposed in the optical path formed by the light guide portion. The optical concentration measuring apparatus may comprise a control IC that drives the light emitting element and performs analog-to-digital conversion of the output signal from the light receiving element. The optical concentration measuring apparatus may comprise a substrate that holds at least one of a light emitting element, a light receiving element, and a control IC. Further, the optical concentration measuring apparatus may comprise a gas cell that accommodates the detected gas when the object to be measured is a gas (hereinafter referred to as "detection gas"), that is, when the apparatus is a gas sensor. A part of the light emitted from the light emitting element is absorbed by the detection gas, and the detection signal of the light receiving element fluctuates according to the environmental concentration of the detection gas. The concentration of the detection gas can be measured from the fluctuation of the detection signal of the light receiving element.

Next, the effects of the optical element of this embodiment will be described in detail with reference to the drawings.

Figure 3:
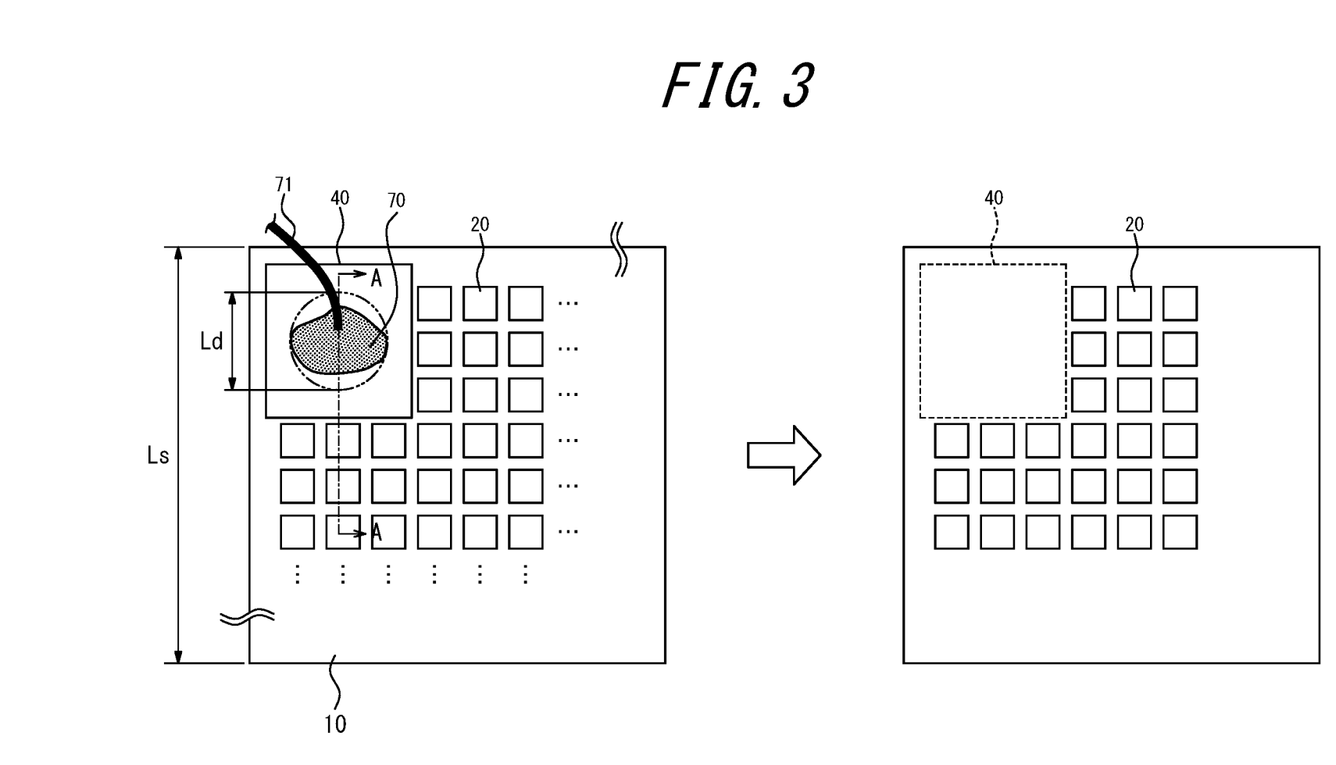
FIG. 3 is a schematic configuration diagram (bird's-eye view) illustrating an example of a conventional optical element.
Figure 4:
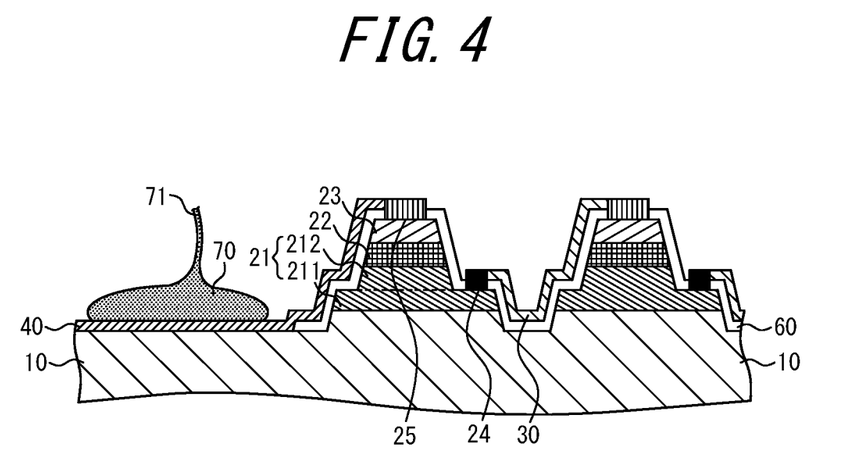
FIG. 4 is a cross-sectional view of the conventional optical element in FIG.3.

FIGS. 3 and 4 illustrate an example (Comparative Example 1) of the conventional optical element. FIG. 3 is a bird's-eye view. FIG. 4 is a cross-sectional view taken along the line A-A illustrated in FIG. 3. Comparative Example 1 comprises the substrate 10, a plurality of unit elements 20, the internal wiring portion 30, the pad electrode 40 and the first insulating portion 50. The unit elements 20 have the first conductive semiconductor layer 21 that includes the first region 211 and the second region 212 placed on the substrate 10, the active layer 22 placed on the second region 212 of the first conductive semiconductor layer 21, the second conductive semiconductor layer 23 placed on the active layer 22, the first contact electrode portion 24 on the first region 211 of the first conductive semiconductor layer 21, and the second contact electrode portion 25 of the second conductive semiconductor layer 23. The internal wiring portion 30 electrically connects the first contact electrode portion 24 of one unit element 20 and the second contact electrode portion 25 of another unit element 20. The pad electrode 40 is electrically connected to the second contact electrode portion 25. As with FIG. 1, the internal wiring portion 30 and the first insulating portion 50 are not illustrated in FIG. 3.

Further, the pad electrode 40 is adjacent to or close to the flat portion of the substrate 10, no mesa structure is formed between the pad electrode 40 and the substrate 10, and no unit element 20 is provided. The conventional optical element further comprises the connection portion 70 for electrically connecting to the outside. The connection portion 70 is bonded to the pad electrode 40.

Figure 11:
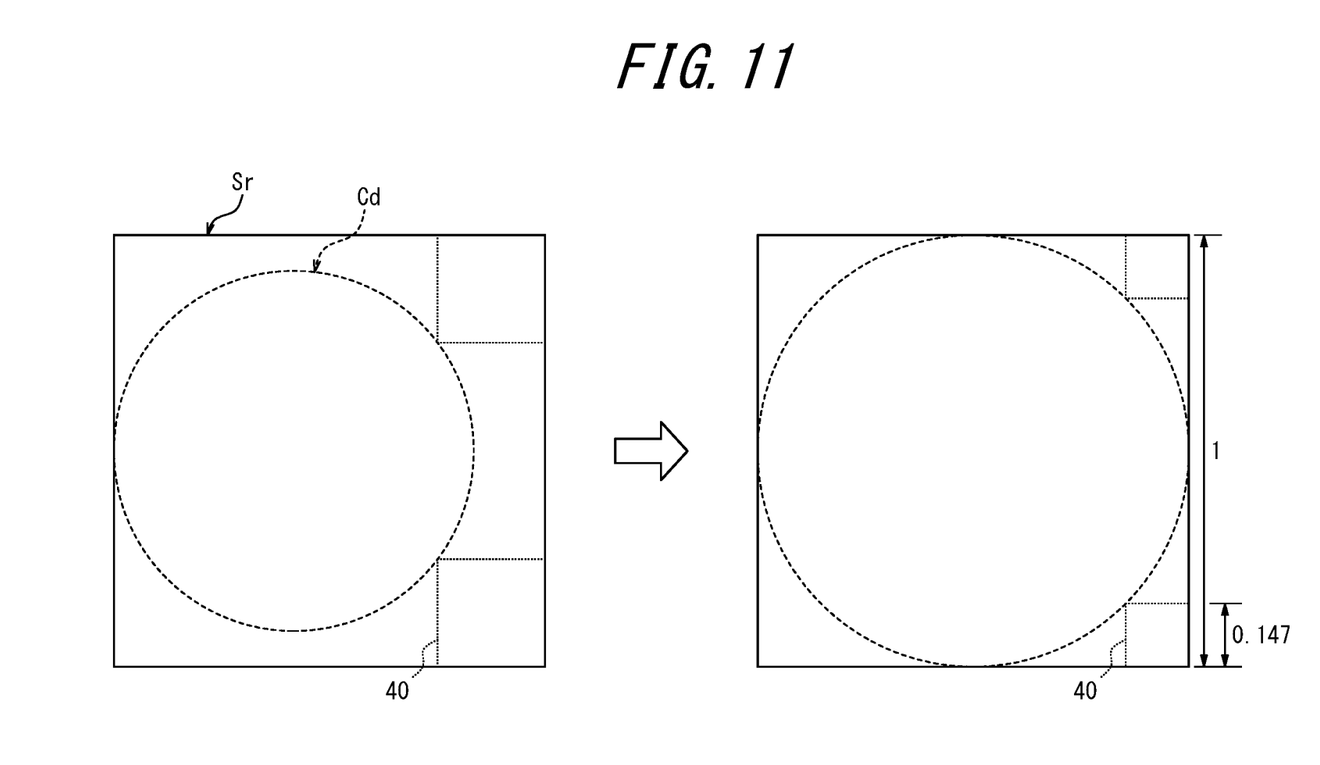
FIG. 11 is a diagram illustrating a relationship between a region of a pad electrode and the circle Cd.

The pad electrode 40 placed on the substrate 10 is formed larger than the diameter Ld of the circle circumscribed to the region where the connection portion 70 and the pad electrode 40 are in contact with each other, in consideration of wire bonding or flip chip bonding misalignment. In the conventional optical elements, the unit element 20 cannot be placed in the region where the pad electrode 40 is formed, so the light emitting region Se or the light receiving region Sr of the optical element has a rectangular shape with one corner missing for the region of the pad electrode 40. As described above, in the conventional optical element, the light receiving region Sr and the light emitting region Se are not rectangular and have an odd-looking shape. Therefore, the circle Cd becomes small, the light emitting area in the circle Ce becomes small, and the size that can be effectively used as an optical element becomes small. In other words, as a result, it has been difficult to design a gas sensor with high fluctuation resistance. Here, as illustrated in FIG. 11, in the optical element having at least two or more pad electrodes 40, when the length of one side of the pad electrode 40 is less than 14.7% the length of the short side Ls of the substrate 10, its inscribed circle is already maximized, so even if the portion missing from the rectangular shape (the region for the pad electrode 40) is reduced, the size of its inscribed circle cannot be increased. However, when the length of one side of the pad electrode 40 is 14.7% or more of the length of the short side Ls of the substrate 10, its inscribed circle can be made larger by reducing the portion missing from the rectangular shape (the region for the pad electrode 40). In other words, the size of the circle Cd is increased relative to the light receiving region Sr. Further, the size of the light emitting region Se is increased relative to the circle Ce. In the conventional optical element, a large pad electrode 40 is used in consideration of wire bonding or flip chip bonding misalignment and concentration of impact force applied. Therefore, it has been difficult to keep it less than 14.7% of the length of the short side Ls of the substrate 10. With the above configuration, the optical element according to this embodiment can reduce the portion (region for the pad electrode 40) missing from the rectangular shape of the light receiving region Sr and the light emitting region Se. In other words, the unit element 20 can also be placed below the pad electrode 40, the portion missing from the rectangular shape can be substantially eliminated (or at least reduced) regardless of the size of the pad electrode 40. Thus, the optical element according to this embodiment can realize a gas sensor having high fluctuation resistance by increasing the effective light receiving region or light emitting region without increasing the chip size.

Figure 5:
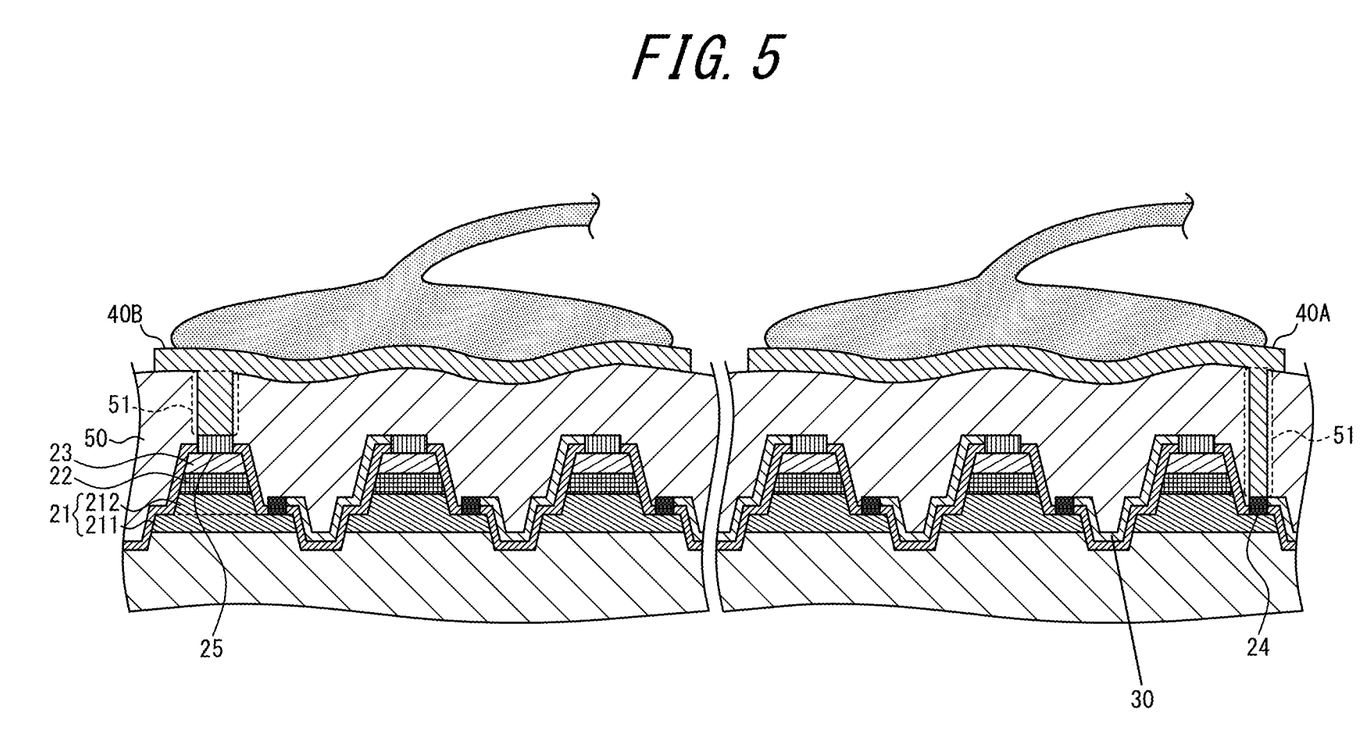
FIG. 5 is a cross-sectional view illustrating an optical element according to a second embodiment.

FIG. 5 illustrates a cross-sectional view of the optical element according to the second embodiment. The optical element according to the second embodiment has a first pad electrode 40A and a second pad electrode 40B. The first contact electrode portion 24 and the first pad electrode 40A are electrically connected to each other via the through hole 51 on the first contact electrode portion 24 of the first insulating portion 50, and the second contact electrode portion 25 and the second pad electrode 40B are electrically connected to each other via the through hole 51 on the second contact electrode portion 25 of the first insulating portion 50. The first pad electrode 40A and the second pad electrode 40B are electrically connected to each other via at least one internal wiring portion 30 and the unit element 20.

In the second embodiment configured as described above, as with FIG. 1, the unit elements 20 can be spread below the pad electrode 40. Thus, the areas of the light receiving region Sr and the light emitting region Se can be used efficiently without waste, and the size of the circle Cd is increased. Further, the light emitting area in the circle Ce is increased, and an area that can be effectively used as an optical element can be increased. As a result, a gas sensor having a high fluctuation resistance can be realized. Along with that, a light path can be designed easily.

Figure 6:
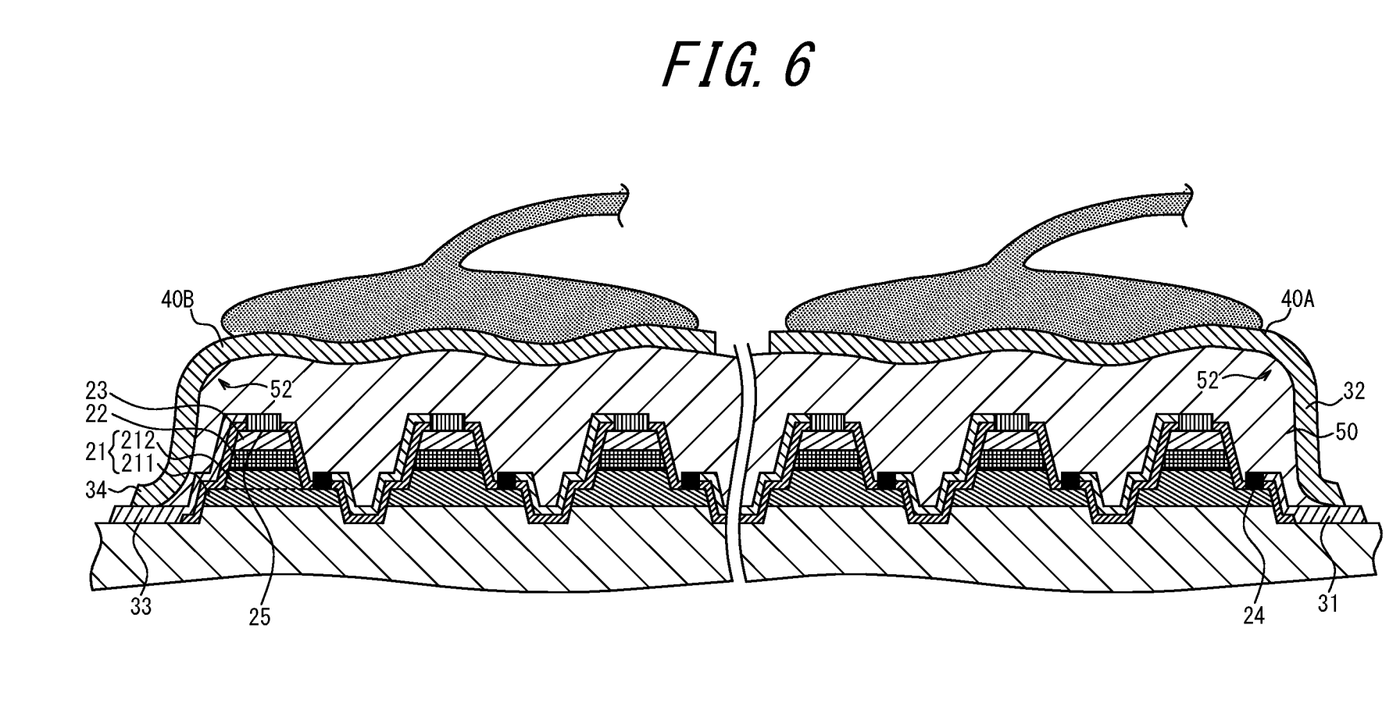
FIG. 6 is a cross-sectional view illustrating an optical element according to a third embodiment.

FIG. 6 illustrates a cross-sectional view of the optical element according to the third embodiment. The optical elements according to the first embodiment and the second embodiment are configured to use the through hole 51 to electrically connect the pad electrode 40 (through hole connection type), whereas the optical element according to the third embodiment is configured to electrically connect the pad electrode 40 at the end of the first insulating portion 50 (insulating portion end connection type). The optical element according to the third embodiment has a first pad electrode 40A and a second pad electrode 40B. The first contact electrode portion 24 and the first pad electrode 40A are electrically connected via a first electrode region 31 placed on the substrate 10 and electrically connected to the first contact electrode portion 24 and a second electrode region 32 placed so as to cover an end 52 of the first insulating portion 50 and electrically connected to the first pad electrode 40A. The second contact electrode portion 25 and the second pad electrode 40B are electrically connected via a third electrode region 33 placed on the substrate 10 and electrically connected to the second contact electrode portion 25 and a fourth electrode region 34 placed so as to cover an end 52 of the first insulating portion 50 and electrically connected to the second pad electrode 40B.

The substrate 10 and the first and third electrode regions 31 and 33 may not be in direct contact with each other, and a second insulating portion 60 made of an insulating material may be formed between them.

Since the connection portion 70 is not bonded to the first electrode region 31 and the third electrode region 33, they can be formed smaller than the pad electrode 40 of Comparative Example 1. Therefore, the unit elements 20 are spread in the substrate 10, and the light emitting region Se or the light receiving region Sr can be effectively utilized without increasing the size of the chip.

Figure 7:
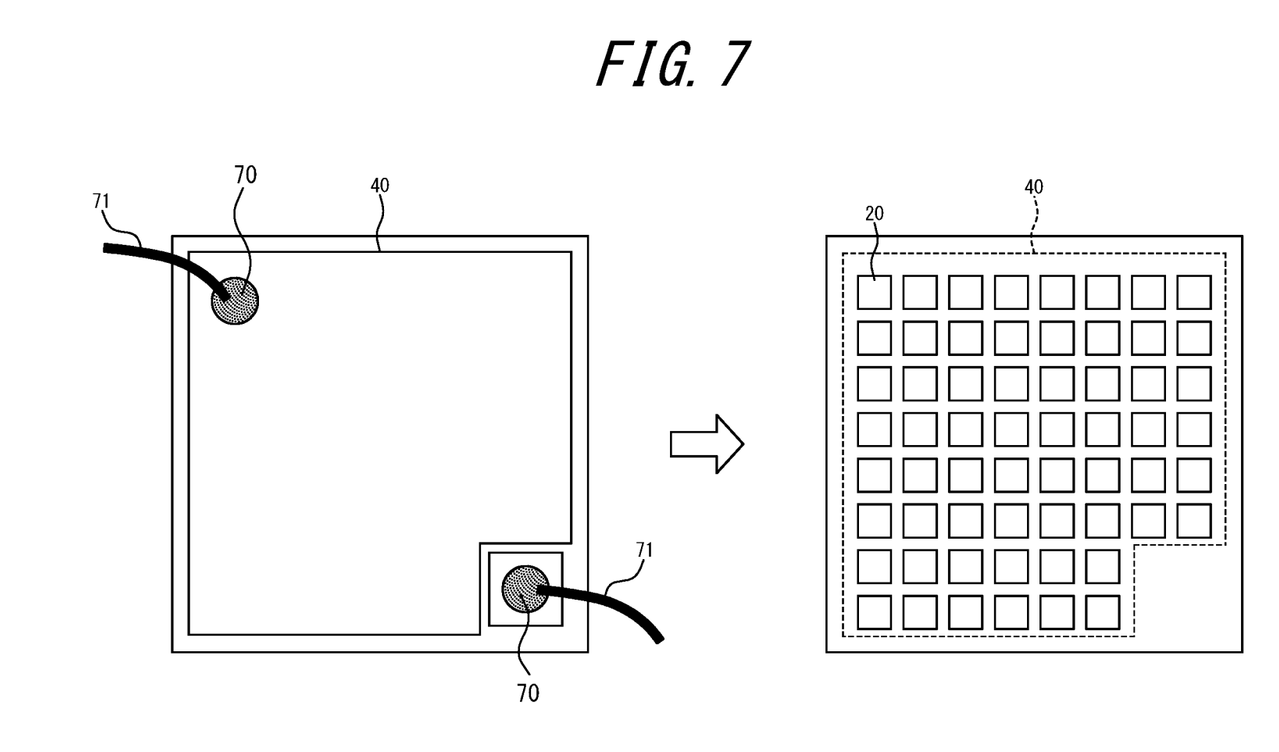
FIG. 7 is a bird's-eye view illustrating an optical element according to a fourth embodiment.

FIG. 7 illustrates a bird's-eye view of the optical element according to the fourth embodiment. As with FIG. 1, the internal wiring portion 30 and the first insulating portion 50 are not illustrated in FIG. 7. In the fourth embodiment, the first pad electrode 40A electrically connected to the first contact electrode portion 24 is placed so that it covers all of the unit elements 20. In the same manner, the second pad electrode 40B electrically connected to the second contact electrode portion 25 may be placed so that it covers all of the unit elements 20. Placing to cover all of the unit elements 20 means that all of the unit elements 20 are contained in a bird's-eye view of the substrate 10 viewed from a distance in the direction perpendicular to the substrate 10.

In order to prevent parasitic capacitance from occurring between the contact electrode and the pad electrode 40 placed in close proximity to each other and affecting the operation of the optical element, it is desirable to cover 50% or more of the unit elements with the pad electrode 40 that has the same potential. Preferably, 80% or more of the unit elements 20 are covered with the pad electrode 40 that has the same potential. More preferably, all of the unit elements 20 are covered.

The invention claimed is:

1. An optical element comprising a substrate, a plurality of unit elements, an internal wiring portion, a pad electrode and a first insulating portion, the unit elements having:
    a first conductive semiconductor layer including a first region and a second region placed on the substrate;
    an active layer placed on the second region of the first conductive semiconductor layer;
    a second conductive semiconductor layer placed on the active layer;
    a first contact electrode portion on the first region of the first conductive semiconductor layer; and
    a second contact electrode portion on the second conductive semiconductor layer, wherein
    the internal wiring portion electrically connects the first contact electrode portion of one of the unit elements and the second contact electrode portion of another unit element;
    the second region, the active layer and the second conductive semiconductor layer form a mesa structure;
    the pad electrode is placed so as to cover the unit elements and is electrically connected to at least one of the first contact electrode portion and the second contact electrode portion; and
    the first insulating portion is placed between the internal wiring portion and the pad electrode so that the internal wiring portion does not contact the pad electrode,
    the optical element further comprising a connection portion placed on the pad electrode to electrically connect to an outside, and electrically connected to the pad electrode, wherein
    a diameter of a circle inscribed to a region where the pad electrode and the connection portion are in contact with each other is 15% or more of a length of a short side of the substrate.

2. The optical element according to claim 1, wherein
    the pad electrode is a first pad electrode connected to the first contact electrode portion; and
    the first contact electrode portion and the first pad electrode are electrically connected to each other through a through hole on the first contact electrode portion of the first insulating portion.

3. The optical element according to claim 1, wherein
    the pad electrode is a second pad electrode connected to the second contact electrode portion; and
    the second contact electrode portion and the second pad electrode are electrically connected to each other through a through hole on the second contact electrode portion of the first insulating portion.

4. The optical element according to claim 1, wherein
    the pad electrode is a first pad electrode connected to the first contact electrode portion and a second pad electrode connected to the second contact electrode portion;

the first contact electrode portion and the first pad electrode are electrically connected to each other through a through hole on the first contact electrode portion of the first insulating portion;

the second contact electrode portion and the second pad electrode are electrically connected to each other through a through hole on the second contact electrode portion of the first insulating portion; and the first pad electrode and the second pad electrode are electrically connected to each other through one or more of the internal wiring portions and the unit elements.

5. The optical element according to claim 1, wherein the pad electrode is a first pad electrode connected to the first contact electrode portion; and the first contact electrode portion and the first pad electrode are electrically connected to each other through a first electrode region placed on the substrate and electrically connected to the first contact electrode portion and a second electrode region placed so as to cover an end of the first insulating portion and electrically connected to the first pad electrode.

6. The optical element according to claim 1, wherein the pad electrode is a second pad electrode connected to the second contact electrode portion; and the second contact electrode portion and the second pad electrode are electrically connected to each other through a third electrode region placed on the substrate and electrically connected to the second contact electrode portion and a fourth electrode region placed so as to cover an end of the first insulating portion and electrically connected to the second pad electrode.

7. The optical element according to claim 1, wherein the pad electrode is a first pad electrode connected to the first contact electrode portion and a second pad electrode connected to the second contact electrode portion;

the first contact electrode portion and the first pad electrode are electrically connected to each other through a first electrode region placed on the substrate and electrically connected to the first contact electrode portion and a second electrode region placed so as to cover an end of the first insulating portion and electrically connected to the first pad electrode; and the second contact electrode portion and the second pad electrode are electrically connected to each other through a third electrode region placed on the substrate and electrically connected to the second contact electrode portion and a fourth electrode region placed so as to cover an end of the first insulating portion and electrically connected to the second pad electrode.

8. The optical element according to claim 1, wherein the pad electrode is placed so as to cover 50% or more of an area of at least two or more of the unit elements.

9. The optical element according to claim 1, wherein the pad electrode is a first pad electrode connected to the first contact electrode portion and is placed so as to cover 50% or more of the unit elements.

10. The optical element according to claim 1, wherein the pad electrode is a second pad electrode connected to the second contact electrode portion and is placed so as to cover 50% or more of the unit elements.

11. The optical element according to claim 1, wherein the pad electrode has an uneven shape corresponding to a shape of the unit element.

12. The optical element according to claim 1, wherein the active layer includes In and Sb as a constituent element.

13. The optical element according to claim 1, wherein the optical element is a light receiving element; and a surface on a side on which the first conductive semiconductor layer of the substrate is not placed is a light incident surface.

14. The optical element according to claim 1, wherein the optical element is a light emitting element; and a surface on a side on which the first conductive semiconductor layer of the substrate is not placed is a light emitting surface.

15. An optical concentration measuring apparatus comprising:

an optical element according to claim 13, which is a light receiving element;

a light emitting element; and a light guide portion that guides light emitted by the light emitting element to the light receiving element, the light guide portion having a light collecting portion; wherein the optical concentration measuring apparatus detects, on the basis of a detection signal output from the light receiving element, concentration of an object to be measured interposed in an optical path formed by the light guide portion.

16. An optical concentration measuring apparatus comprising:

a light receiving element;

an optical element according to claim 14, which is a light emitting element; and a light guide portion that guides light emitted by the light emitting element to the light receiving element, the light guide portion having a light collecting portion, wherein the optical concentration measuring apparatus detects, on the basis of a detection signal output from the light receiving element, concentration of an object to be measured interposed in an optical path formed by the light guide portion.

* * * * *